US010590136B2

(12) United States Patent
Chen et al.

(10) Patent No.: US 10,590,136 B2
(45) Date of Patent: Mar. 17, 2020

(54) PROCESSES FOR THE PREPARATION OF CIS-4-[2-{[(3S,4R)-3-FLUOROOXAN-4-YL] AMINO}-8-(2,4,6-TRICHLOROANILINO)-9H-PURIN-9-YL]-1-METHYLCYCLO HEXANE-1-CARBOXAMIDE

(71) Applicant: Celgene Corporation, Summit, NJ (US)

(72) Inventors: Zheng Chen, Westfield, NJ (US); Maryll Elaine Geherty, Pennington, NJ (US); Matthew Michael Kreilein, Hillsborough, NJ (US); Xiaoling Lu, Whippany, NJ (US); Nanfei Zou, Fanwood, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/150,345

(22) Filed: Oct. 3, 2018

(65) Prior Publication Data

US 2019/0100522 A1  Apr. 4, 2019

Related U.S. Application Data

(60) Provisional application No. 62/568,089, filed on Oct. 4, 2017.

(51) Int. Cl.
*C07D 473/32* (2006.01)
*C07D 407/12* (2006.01)
*A61P 35/00* (2006.01)

(52) U.S. Cl.
CPC ......... *C07D 473/32* (2013.01); *C07D 407/12* (2013.01); *A61P 35/00* (2018.01)

(58) Field of Classification Search
CPC .............................. C07D 407/12; C07D 473/32
USPC ........................................ 544/277, 323, 326
See application file for complete search history.

(56) References Cited

U.S. PATENT DOCUMENTS

| | | | |
|---|---|---|---|
| 4,810,643 A | 3/1989 | Souza | |
| 4,999,291 A | 3/1991 | Souza | |
| 5,229,496 A | 7/1993 | Deeley et al. | |
| 5,391,485 A | 2/1995 | Deeley et al. | |
| 5,393,870 A | 2/1995 | Deeley et al. | |
| 5,580,755 A | 12/1996 | Souza | |
| 5,582,823 A | 12/1996 | Souza | |
| 5,858,968 A | 1/1999 | Weiner et al. | |
| 7,521,446 B2 | 4/2009 | Albers et al. | |
| 7,723,340 B2 | 5/2010 | Albers et al. | |
| 7,759,342 B2 | 7/2010 | Bennett et al. | |
| 8,101,588 B2 | 1/2012 | Albers et al. | |
| 8,158,635 B2 | 4/2012 | Beauchamps et al. | |
| 8,324,225 B2 | 12/2012 | Brain et al. | |
| 8,440,661 B2 | 5/2013 | Bennett et al. | |
| 8,491,930 B2 | 7/2013 | Fernandez De Gatta Garcia et al. | |
| 8,603,527 B2 | 12/2013 | Bhat et al. | |
| 8,680,076 B2 | 3/2014 | Bennett et al. | |
| 9,187,479 B2 | 11/2015 | Clareen et al. | |
| 9,198,866 B2 | 12/2015 | Bhat et al. | |
| 9,512,124 B2 | 12/2016 | Alexander et al. | |
| 9,737,541 B2 | 8/2017 | Alexander | |
| 2003/0191086 A1 | 10/2003 | Hanus et al. | |
| 2007/0142405 A1 | 6/2007 | Dong et al. | |
| 2008/0021048 A1 | 1/2008 | Bennett et al. | |
| 2009/0312320 A1 | 12/2009 | Albers et al. | |
| 2010/0016586 A1 | 1/2010 | Bajji et al. | |
| 2012/0115890 A1 | 5/2012 | Beauchamps et al. | |
| 2012/0129807 A1 | 5/2012 | Bennett et al. | |
| 2013/0034495 A1 | 2/2013 | Beauchamps et al. | |
| 2013/0225564 A1 | 8/2013 | Clareen et al. | |
| 2014/0093566 A1 | 4/2014 | Bhat et al. | |
| 2014/0206697 A1 | 7/2014 | Clareen et al. | |
| 2016/0039822 A1 | 2/2016 | Clareen et al. | |
| 2016/0096841 A1 | 4/2016 | Alexander et al. | |
| 2017/0042902 A1 | 2/2017 | Alexander et al. | |

FOREIGN PATENT DOCUMENTS

| | | |
|---|---|---|
| WO | WO 1999/015155 A1 | 4/1999 |
| WO | WO 2006/076595 A1 | 7/2006 |
| WO | WO 2007/062338 A2 | 5/2007 |
| WO | WO 2007/127382 A1 | 11/2007 |
| WO | WO 2008/057252 A2 | 5/2008 |
| WO | WO 2011/071491 A1 | 6/2011 |
| WO | WO 2014/172616 A2 | 10/2014 |
| WO | WO 2015/086505 A1 | 6/2015 |
| WO | WO 2016/057370 A1 | 4/2016 |

OTHER PUBLICATIONS

Pimlott, PubMed Abstract (Nucl Med Commun., 26(3):183-8), 2005.*
Hulikal, Deuterium Labeled Compounds in Drug Discovery Process, Abstract, 2010.*
U.S. Appl. No. 15/475,836, dated Mar. 31, 2017, Chen et al.
Alcorn et al., "c-Jun N-Terminal Kinase 1 is Required for the Development of Pulmonary Fibrosis," *Am. J. Respir. Cell Mol. Biol.*, 40:422-432 (2009).
Aljaberi et al., "Functional performance of silicified microcrystalline cellulose versus microcrystalline cellulose: a case study," Drug Development and Industrial Pharmacy 35(9): 1066-1071 (2009).
Bollag et al., "Vemurafenib: the first drug approved for BRAF-mutant cancer," *Nat. Rev. Drug Discov.*, 11(11):873-866 (2012).
Cheson et al., "Revised response criteria for malignant lymphoma," *J. Clin. Oncol.*, 25(9):579-586 (2007).

(Continued)

*Primary Examiner* — Deepak R Rao
(74) *Attorney, Agent, or Firm* — Jones Day

(57) ABSTRACT

Provided herein are processes for the preparation of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, or a salt, solvate, hydrate, or isotopologue thereof.

21 Claims, 11 Drawing Sheets

(56) References Cited

OTHER PUBLICATIONS

Figure 1:
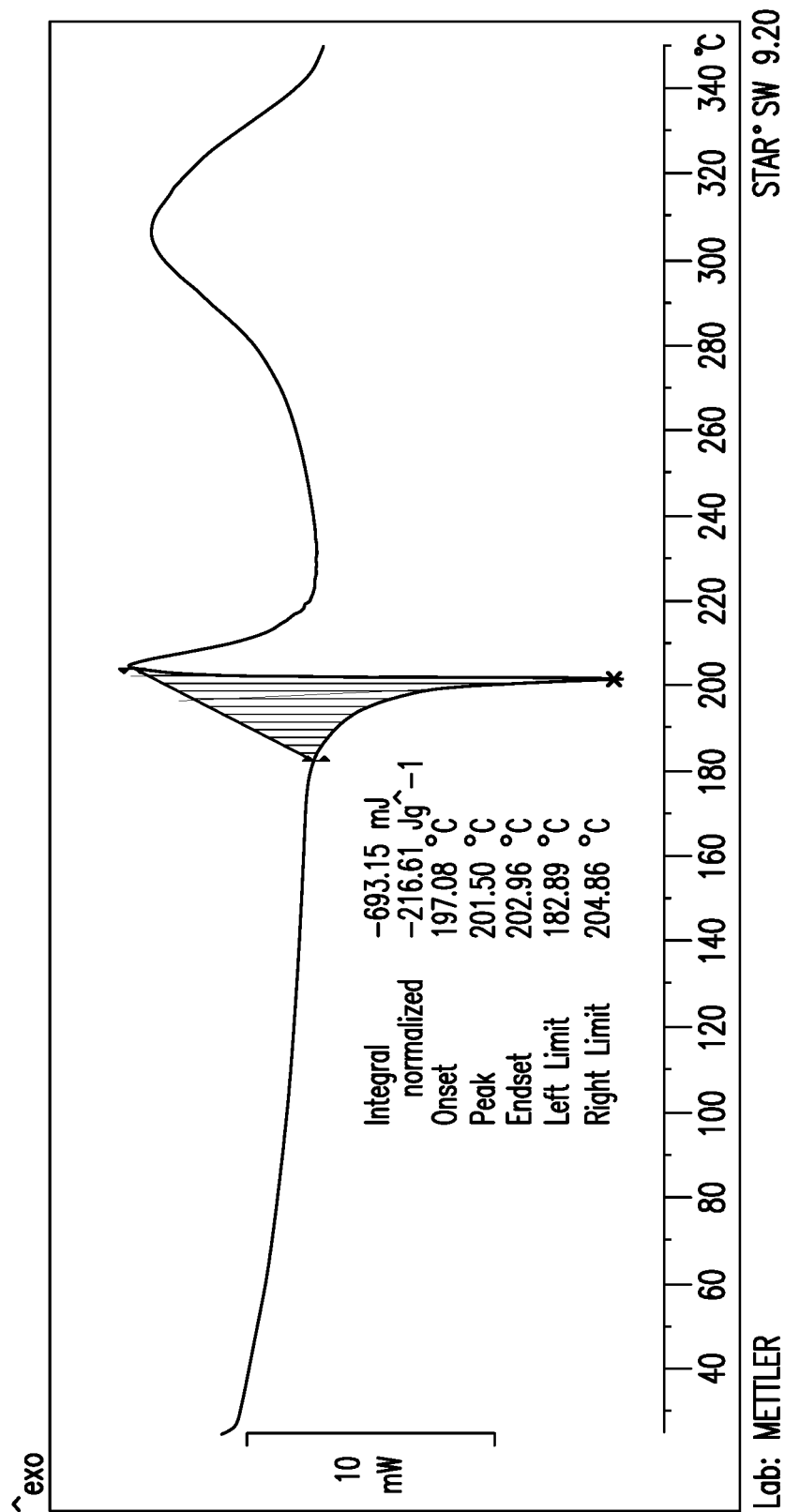

Chen et al., "SKLB-287, a novel oral multikinase inhibitor of EGFR and VEGFR2, exhibits potent antitumor activity in LoVo colorectal tumor model," *Neoplasma,* 61(5):514-522 (2014).
Corcoran et al., "EGFR-mediated re-activation of MAPK signaling contributes to insensitivity of BRAF mutant colorectal cancers to RAF inhibition with vemurafenib," *Cancer Discov.,* 2(3):227-235 (2012).
Davis, "Signal transduction by the JNK group of MAP kinases," *Cell,* 203:239-252 (2000).
Durie et al, "International uniform response criteria for multiple myeloma," *Leukemia,* 20:1467-1473 (2006).
Edge et al., "Polysaccharide engineering: Silicified microcrystalline cellulose as a novel high-functionality pharmaceutical material", in: *Polysaccharide Applications: Cosmetics and Pharmaceuticals,* American Chemical Society Symposium Series 737, Chapter 7, pp. 98-112 (1999).
Eisenhauer et al., "New response evaluation criteria in solid tumours: revised RECIST guideline (version 1.1)," *Eur. J. Cancer,* 45(2):228-247 (2009).
Emens et al., "Chemotherapy: friend of foe to cancer vaccines," *Curr. Opin. Mol. Ther.,* 3(1):77-84 (2001).
Fuchs et al., "Oncogenic β-catenin signaling networks in colorectal cancer," *Cell Cycle,* 4(11):1522-1539 (2005).
Hallek et al., "Guidelines for the diagnosis and treatment of chronic lymphocytic leukemia: a report from the InternationalWorkshop on Chronic Lymphocytic Leukemia updating the National Cancer Institute—Working Group 1996 guidelines," *Blood,* 111(12):5446-5456 (2008).
Kluwe et al., "Modulation of hepatic fibrosis by c-Jun-N-terminal kinase inhibition," *Gastroenterology,* 138:347-359 (2010).
Lee et al., "Bleomycin induces alveolar epithelial cell death through JNK-dependent activation of the mitochondrial death pathway," *Am. J. Physiol. Lung Cell Mol. Physiol.,* 289:L521-l528 (2005).
Lin et al., "Connective tissue growth factor induces collagen I expression in human lung fibroblasts through the Rac1/MLK3/JNK/AP-1 pathway," *Biochim. Biophys. Acta,* 1833:2823-2833 (2013).
MedicineNet, "Definition of Cancer," http://www.MedicineNet.com, 2015 (1 page).
Penichet et al., "Antibody-cytokine fusion proteins for the therapy of cancer," *J. Immunol. Methods,* 284:91-101 (2001).
Roitt et al., Immunology, Third Edition, Mosby, St. Louis, MO, 17.1-17.12 (1993).
Therasse et al., "New guidelines to evaluate the response to treatment in solid tumors," *J. Natl. Cancer Inst.,* 92(3):205-216 (2000).
Tobyn et al., "Physiochemical comparison between microcrystalline cellulose and silicified microcrystalline cellulose," *International Journal of Pharmaceutics* 169(2):183-194 (1998).
Wen et al., "Updated response assessment criteria for high-grade gliomas: response assessment in neuro-oncology working group," *J. Clin. Oncol.,* 28(11):1963-1972 (2010).
Wilen et al., "Strategies in optical resolutions," *Tetrahedron,* 33:2725-2736 (1977).
Wilen, Tables of Resolving Agents and Optical Resolutions, (E.L. Eliel, Ed.), University of Notre Dame Press, Notre Dame, IN, p. 268 (1972).
Yoshida et al., "MAP kinase activation and apoptosis in lung tissues from patients with idiopathic pulmonary fibrosis," *J. Pathol.,* 198:388-396 (2002).

\* cited by examiner

PROCESSES FOR THE PREPARATION OF CIS-4-[2-{[(3S,4R)-3-FLUOROOXAN-4-YL]AMINO}-8-(2,4,6-TRICHLOROANILINO)-9H-PURIN-9-YL]-1-METHYLCYCLOHEXANE-1-CARBOXAMIDE

This application claims the benefit of U.S. Provisional Application No. 62/568,089, filed Oct. 4, 2017, the entire content of which is incorporated herein by reference.

1. FIELD

Provided herein are processes for the preparation of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, or a salt, solvate, hydrate, or isotopologue thereof.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., Immunology, 17.1-17.12 (3rd ed., Mosby, St. Louis, Mo., 1993)).

Cancers figure among the leading causes of death worldwide, accounting for 8.2 million deaths in 2012. It is expected that annual cancer cases will rise from 14 million in 2012 to 22 million within the next two decades (See Cancer Fact sheet No. 297, World Health Organization, February 2014, retrieved 10 June 2014 and Globocan 2012, IARC).

Certain aminopurine compounds have been reported to show pharmaceutical properties suitable for clinical development in the treatment of cancer. Aminopurine compounds can be made using conventional organic syntheses and commercially available starting materials. By way of example and not limitation, aminopurine compounds can be prepared as described in U.S. Pat. Nos. 7,723,340, 8,158,635, and U.S. patent application Ser. No. 14/874,513.

One example of an aminopurine compound with therapeutic potential is cis-4-[2-{[(3 S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide. The compound and a process of synthesizing the compound are described in U.S. Pat. No. 9,512,124, which is incorporated herein by reference in its entirety.

Despite its current availability, a need still exists for the development of alternative synthetic processes for preparing (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide useful for multi-kg production of the compound.

3. SUMMARY

Provided herein is a process for preparing a compound of Formula (I):

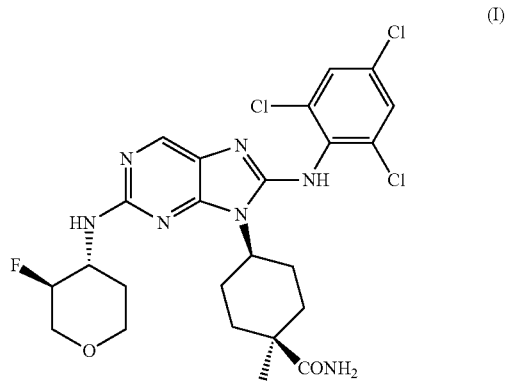 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

or a salt, solvate, hydrate, or isotopologue thereof, comprising (a) contacting Compound 1 of the formula:

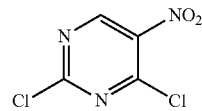

or a salt, solvate, hydrate, or isotopologue thereof, with Compound 2 of the Formula:

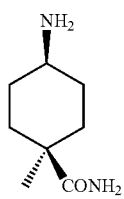

or a salt, solvate, hydrate, or isotopologue thereof, to provide Compound 3 of the Formula:

3

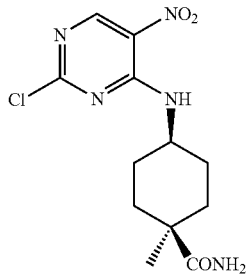

or a solvate, hydrate, or isotopologue thereof;

(b) contacting Compound 3, or a solvate, hydrate, or isotopologue thereof, with Compound 4 of the Formula:

4

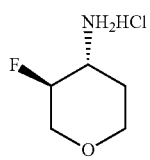

or a solvate, hydrate, or isotopologue thereof, to provide Compound 5 of the Formula:

5

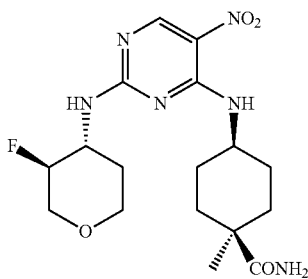

or a solvate, hydrate, or isotopologue thereof;

(c) reducing Compound 5, or a solvate, hydrate, or isotopologue thereof with a reducing agent and a catalyst, to provide Compound 6 of the Formula:

6

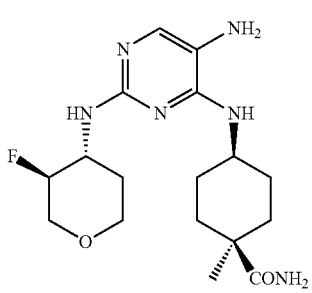

or a salt, solvate, hydrate, or isotopologue thereof;

(d) contacting Compound 6 or a solvate, hydrate, or isotopologue thereof, with 2,4,6-trichlorophenyl isothiocyanate, to provide Compound 7 of the Formula:

7

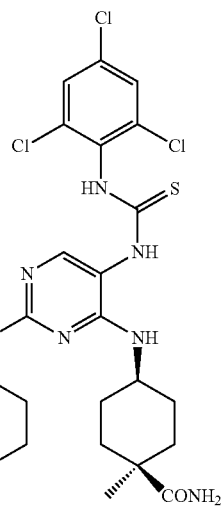

or a solvate, hydrate, or isotopologue thereof;

(e) contacting Compound 7 or a solvate, hydrate, or isotopologue thereof with ethylcarbodiimide hydrochloride, to provide a compound of Formula (I), or a solvate, hydrate, or isotopologue thereof; and (f) optionally converting the compound of Formula (I), or a solvate, hydrate, or isotopologue thereof, to a citrate salt of the compound of Formula (I).

In certain embodiments, provided herein is a process for preparing a compound of Formula (I):

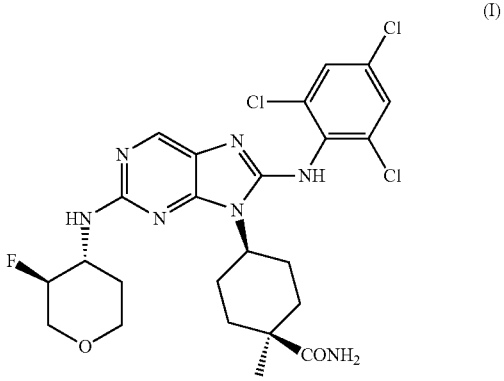 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

(I)

or a salt, solvate, hydrate, or isotopologue thereof, comprising (e) contacting Compound 7 or a solvate, hydrate, or isotopologue thereof with ethylcarbodiimide hydrochloride, to provide a compound of Formula (I), or a solvate, hydrate, or isotopologue thereof; and (f) optionally converting the compound of Formula (I), or a solvate, hydrate, or isotopologue thereof, to a citrate salt of the compound of Formula (I).

In certain embodiments, provided herein is a process for preparing Compound 7:

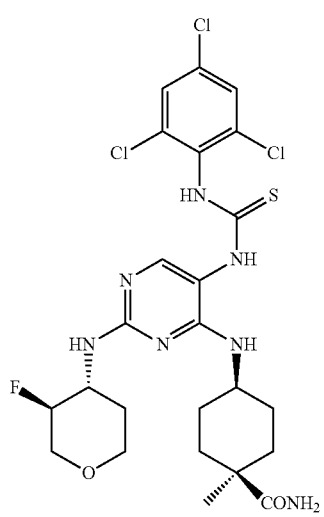

or a salt, solvate, hydrate, or isotopologue thereof, comprising (d) contacting Compound 6 or a solvate, hydrate, or isotopologue thereof, with 2,4,6-trichlorophenyl isothiocyanate.

In certain embodiments, provided herein is a process for preparing Compound 6:

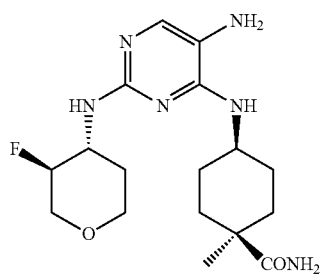

or a salt, solvate, hydrate, or isotopologue thereof, comprising (c) reducing Compound 5, or a solvate, hydrate, or isotopologue thereof with a reducing agent and a catalyst.

In certain embodiments, provided herein is a process for preparing Compound 5

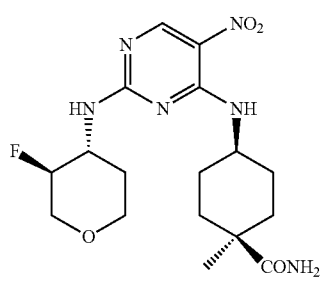

or a salt, solvate, hydrate, or isotopologue thereof, comprising (b) contacting Compound 3, or a solvate, hydrate, or isotopologue thereof, with Compound 4 or a solvate, hydrate, or isotopologue thereof.

In certain embodiments, provided herein is a process for preparing Compound 3:

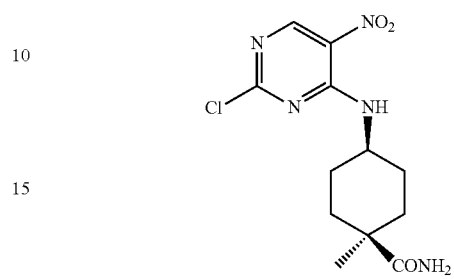

or a salt, solvate, hydrate, or isotopologue thereof, comprising (a) contacting Compound 1 of the Formula:

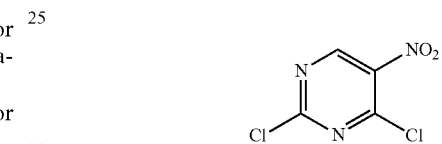

or a solvate, hydrate, or isotopologue thereof, with Compound 2 of the Formula:

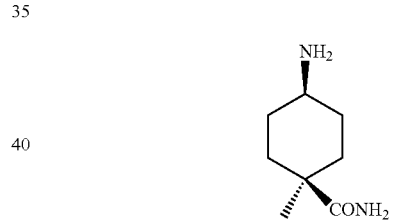

or a solvate, hydrate, or isotopologue thereof.

4. BRIEF DESCRIPTION OF THE FIGURES

FIG. 1 provides a representative differential scanning calorimetric (DSC) thermogram of Compound 3.

Figure 2:
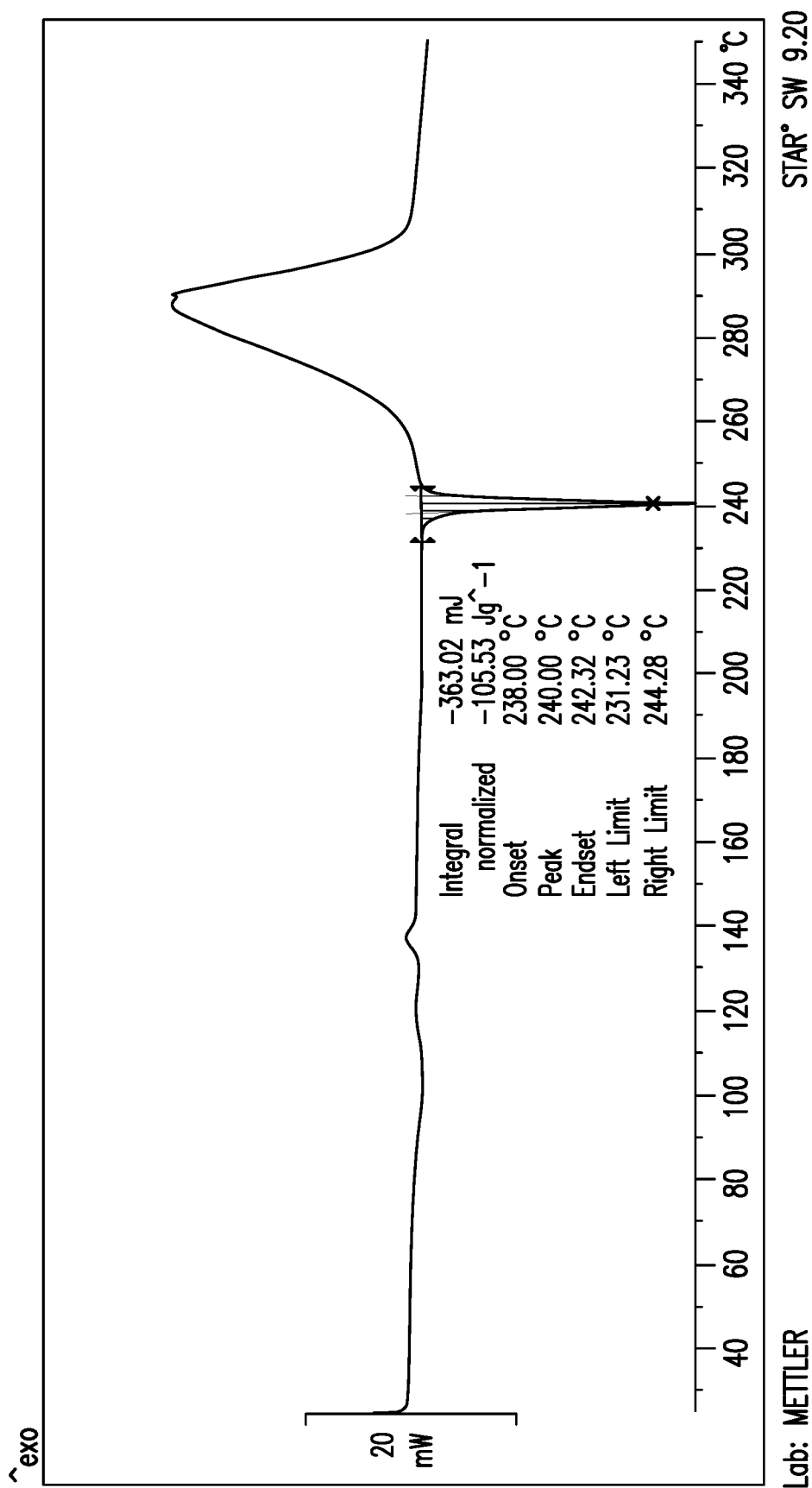

FIG. 2 provides a representative DSC thermogram of Compound 5.

Figure 3:
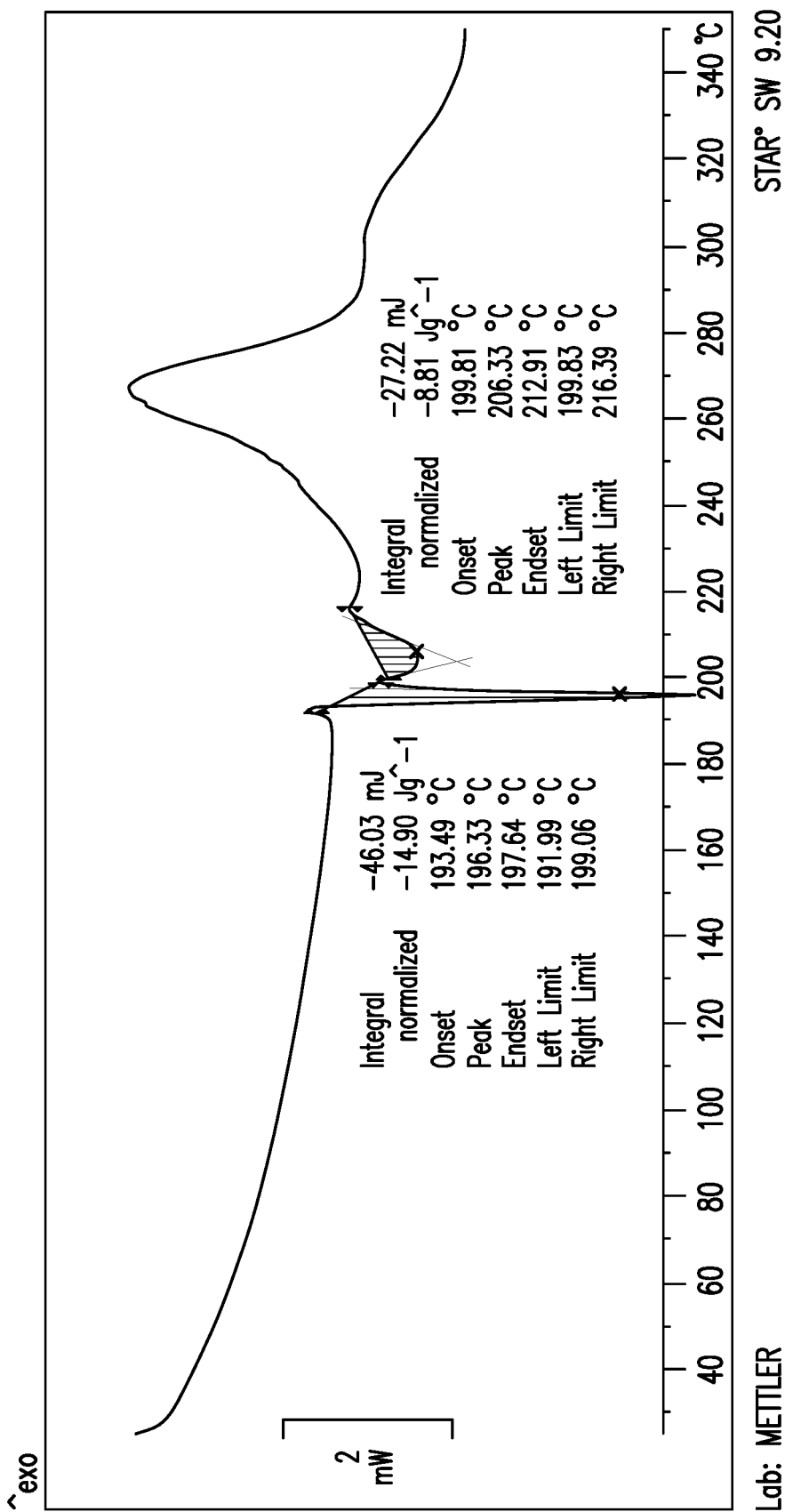

FIG. 3 provides a representative DSC thermogram of Compound 7.

Figure 4:
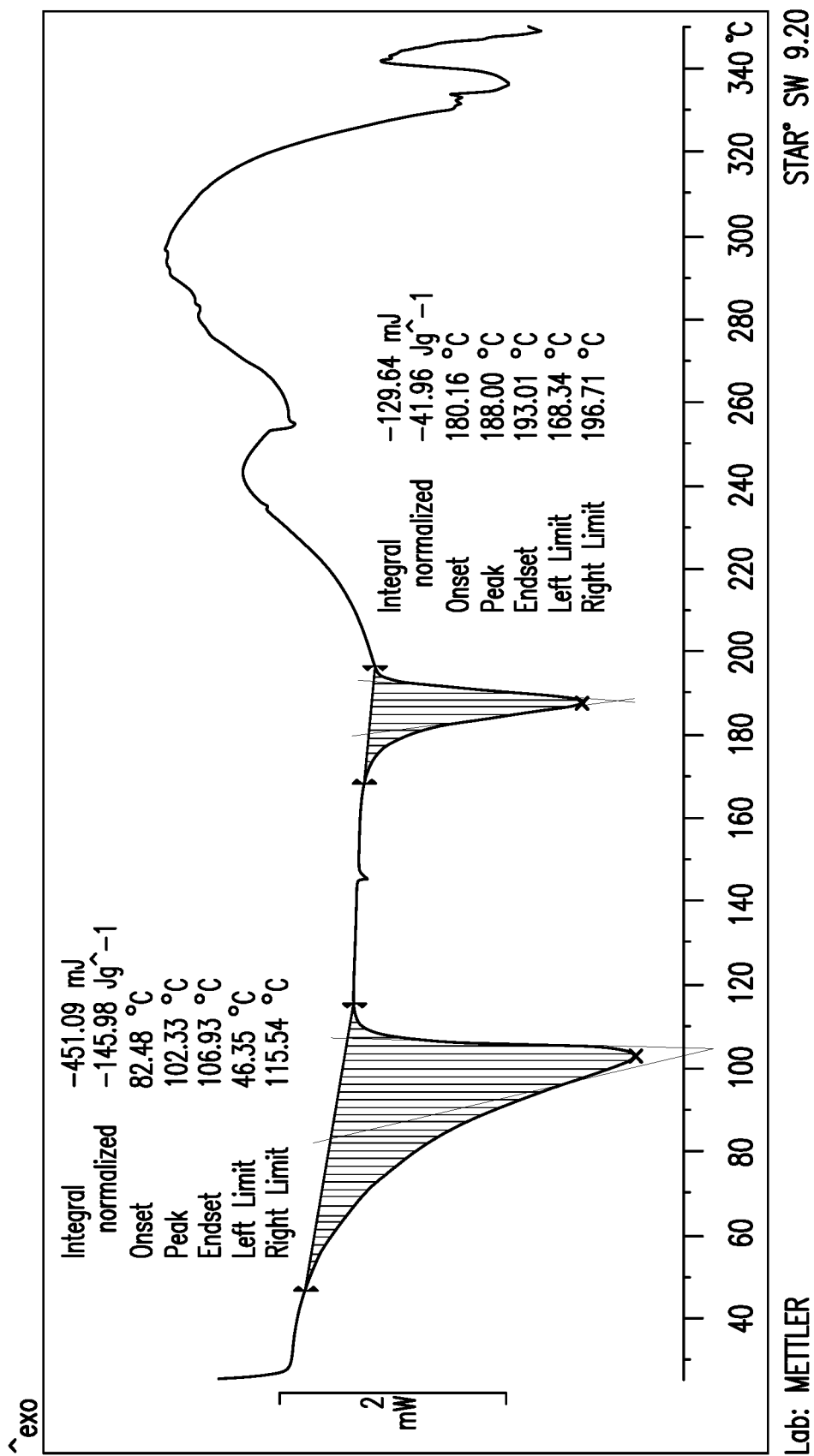

FIG. 4 provides a representative DSC thermogram of a compound of Formula (I).

Figure 5:
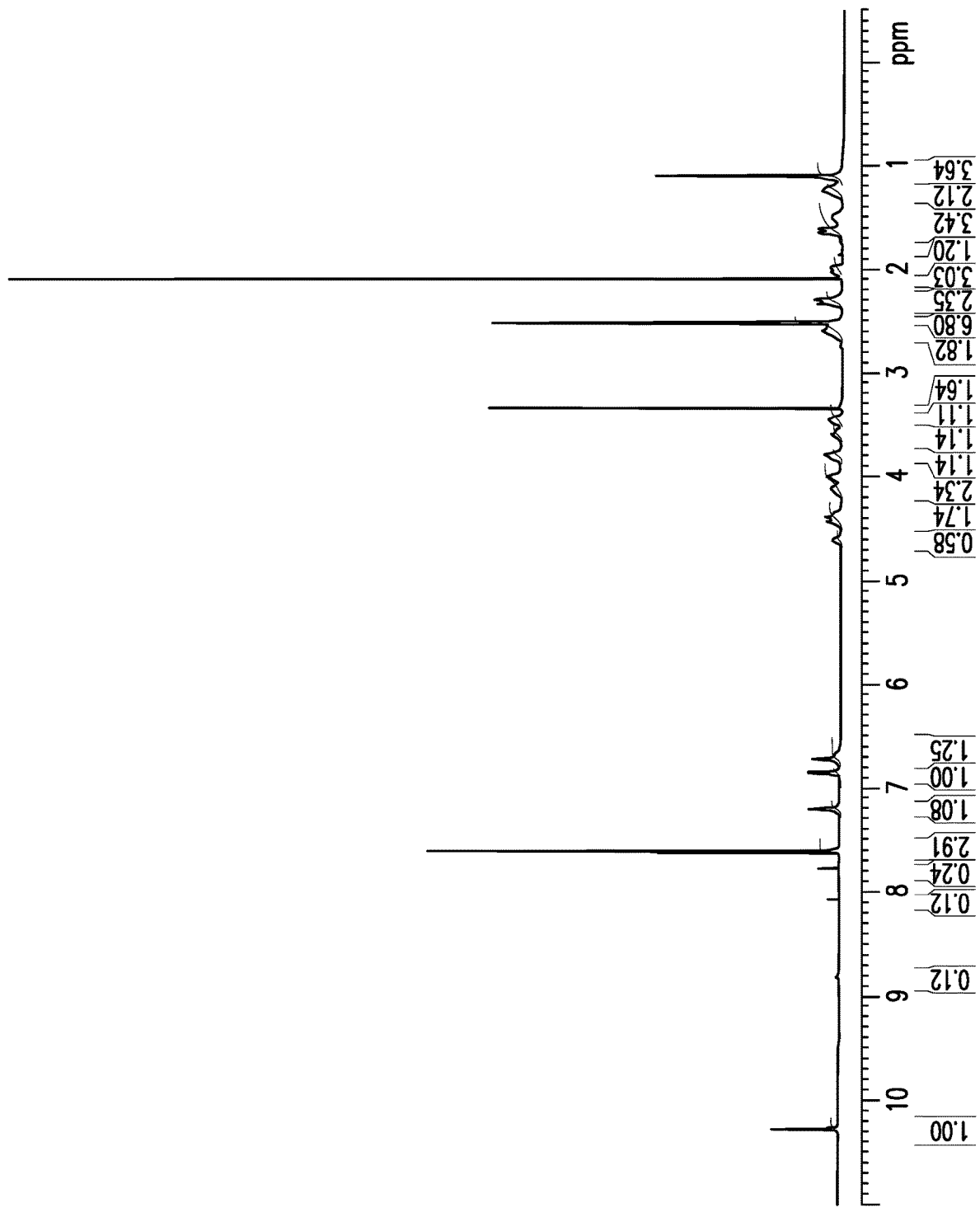

FIG. 5 provides a Nuclear Magnetic Resonance (NMR) spectrum for a compound of Formula (I).

Figure 6:
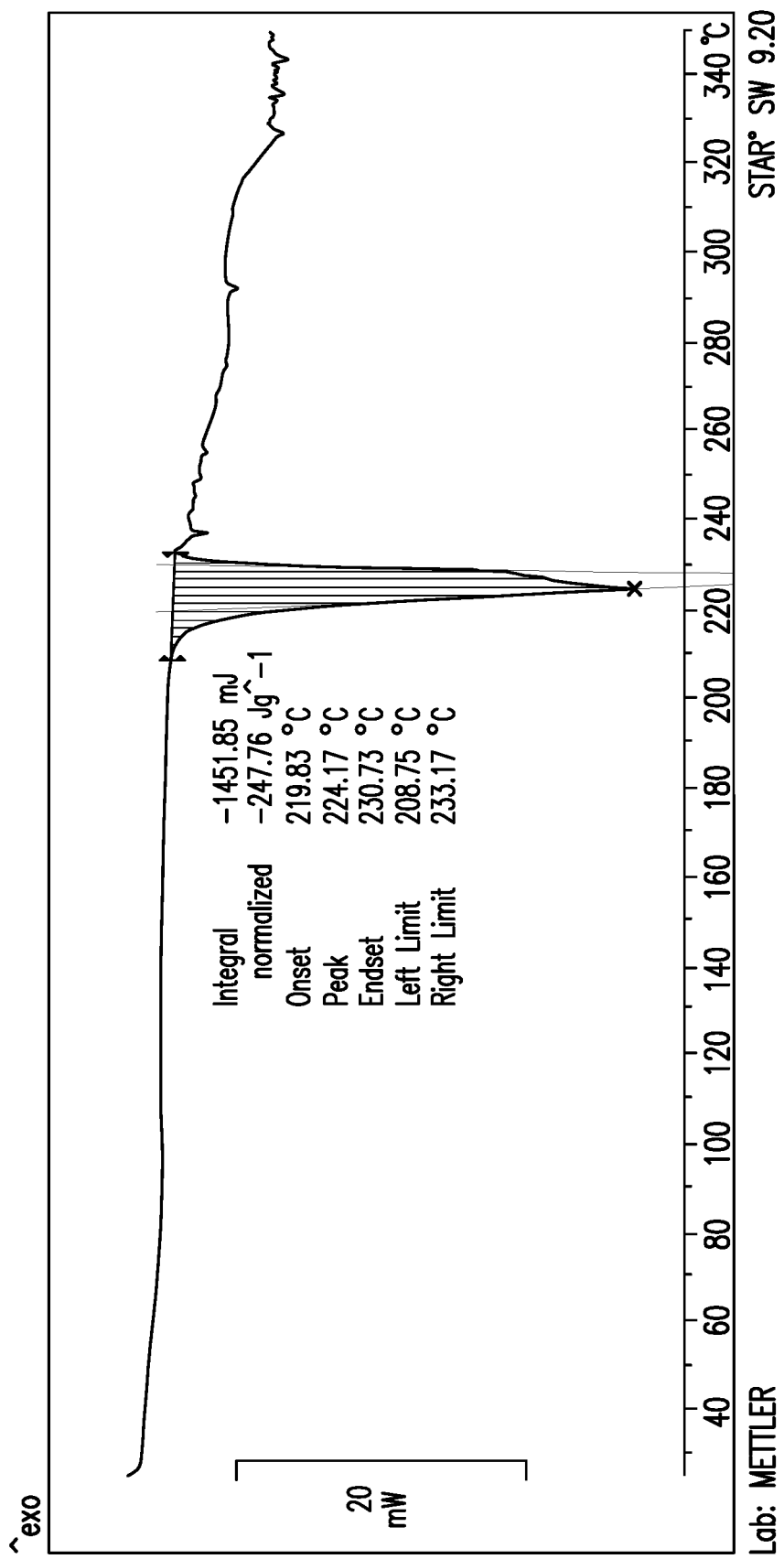

FIG. 6 provides a representative DSC thermogram for the citrate salt of a compound of Formula (I).

Figure 7:
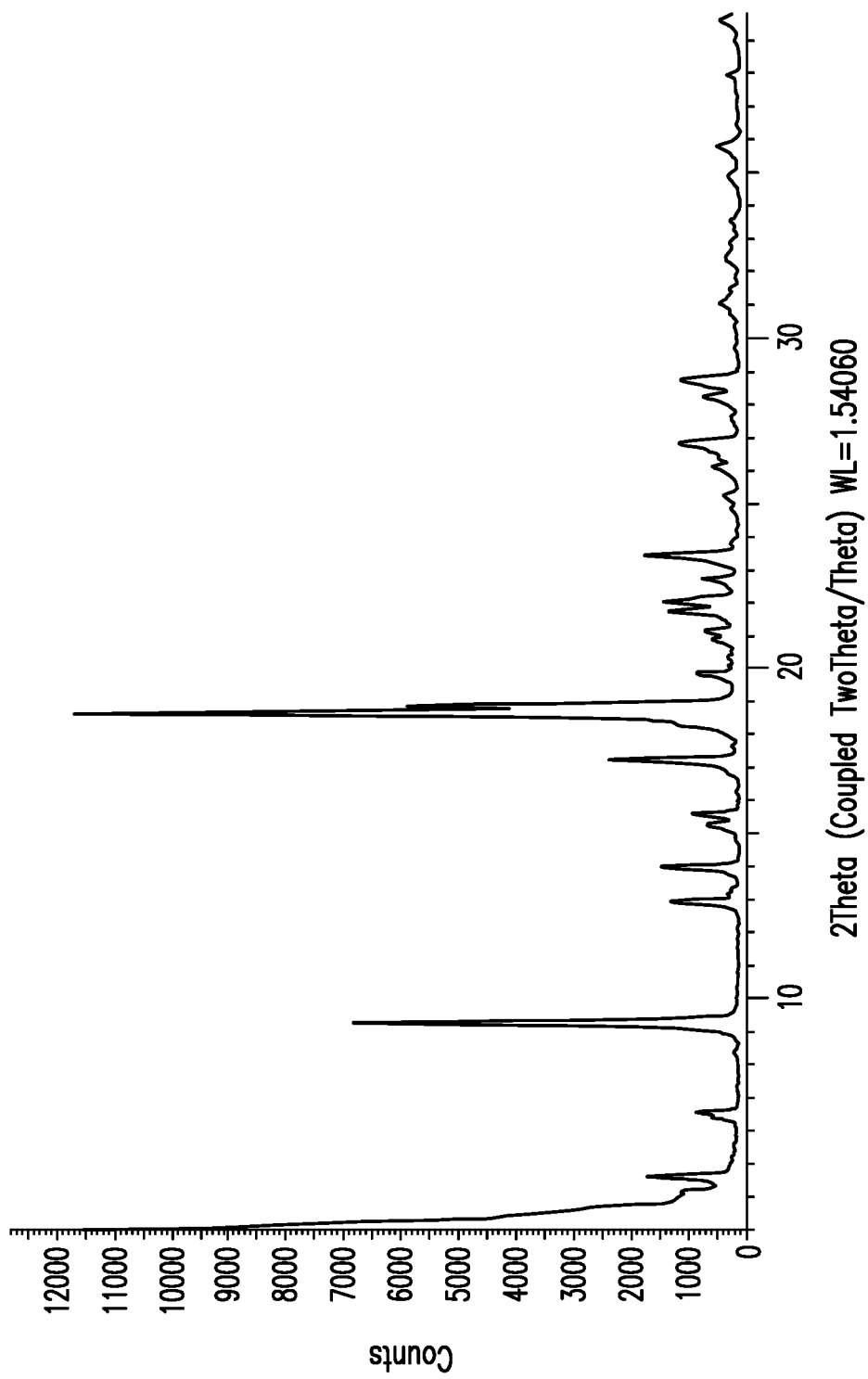

FIG. 7 provides a representative XRPD pattern of the citrate salt of a compound of Formula (I).

Figure 8:
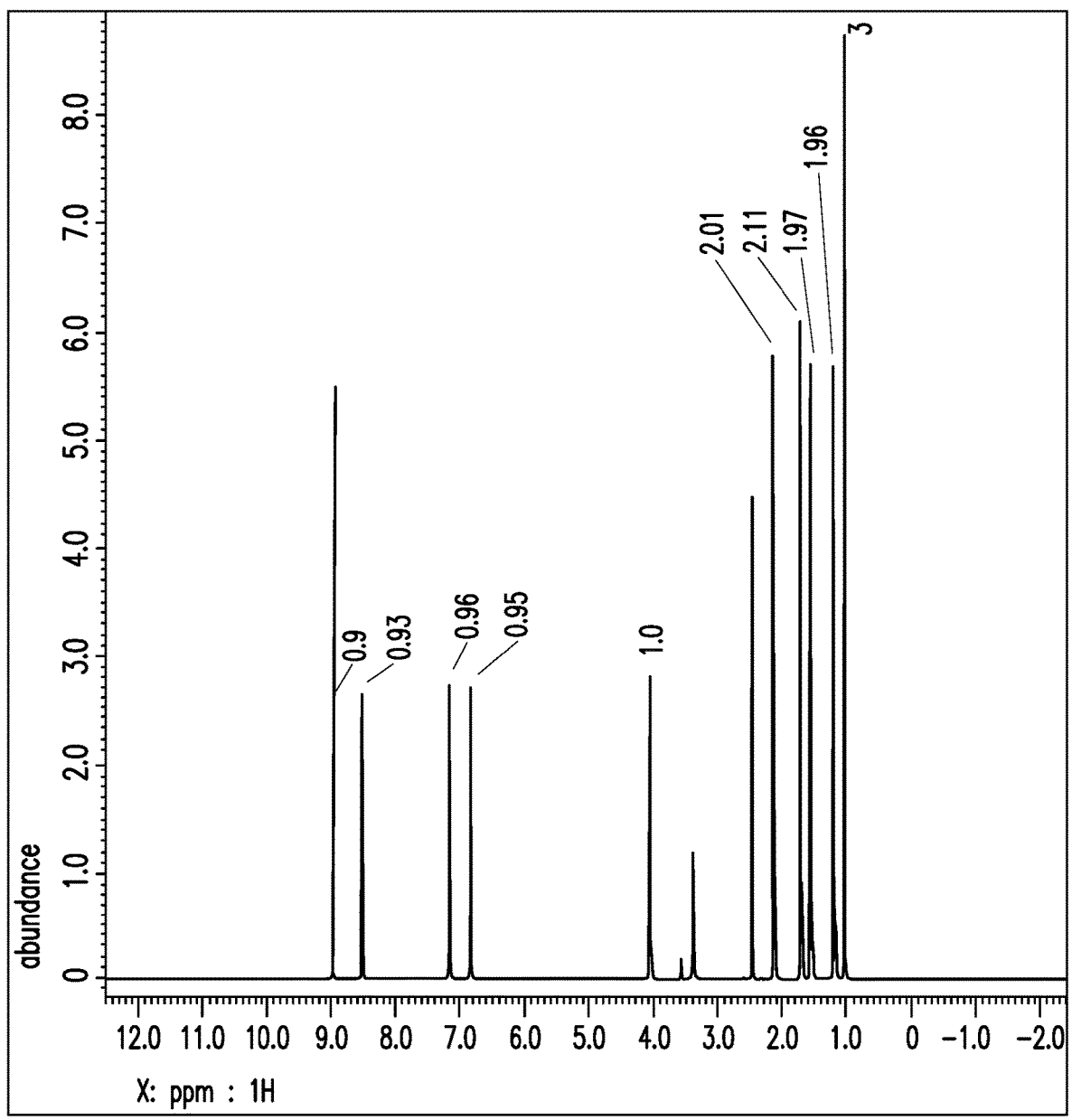

FIG. 8 provides a proton NMR spectrum for Compound 3.

Figure 9:
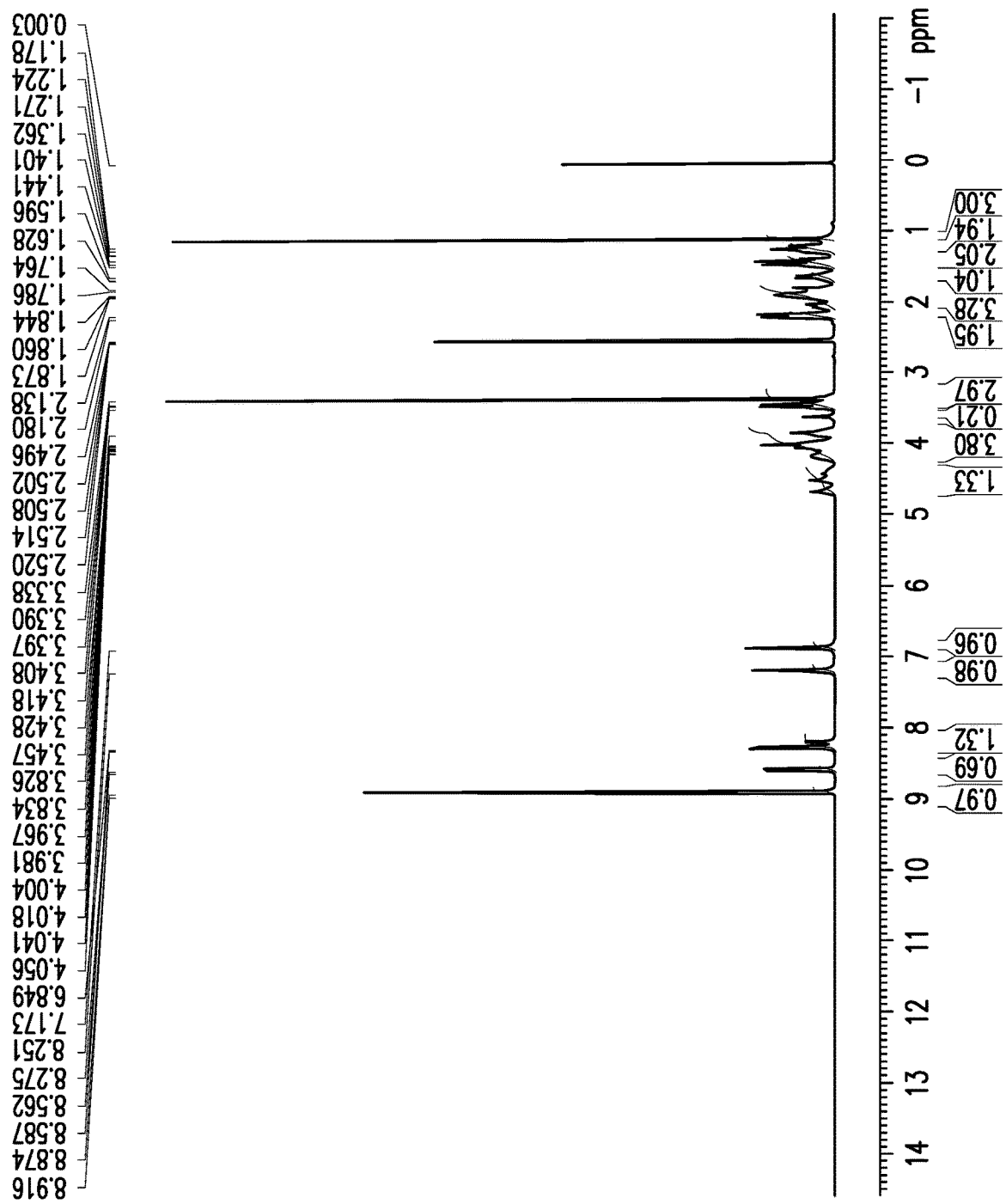

FIG. 9 provides a proton NMR spectrum for Compound 5.

Figure 10:
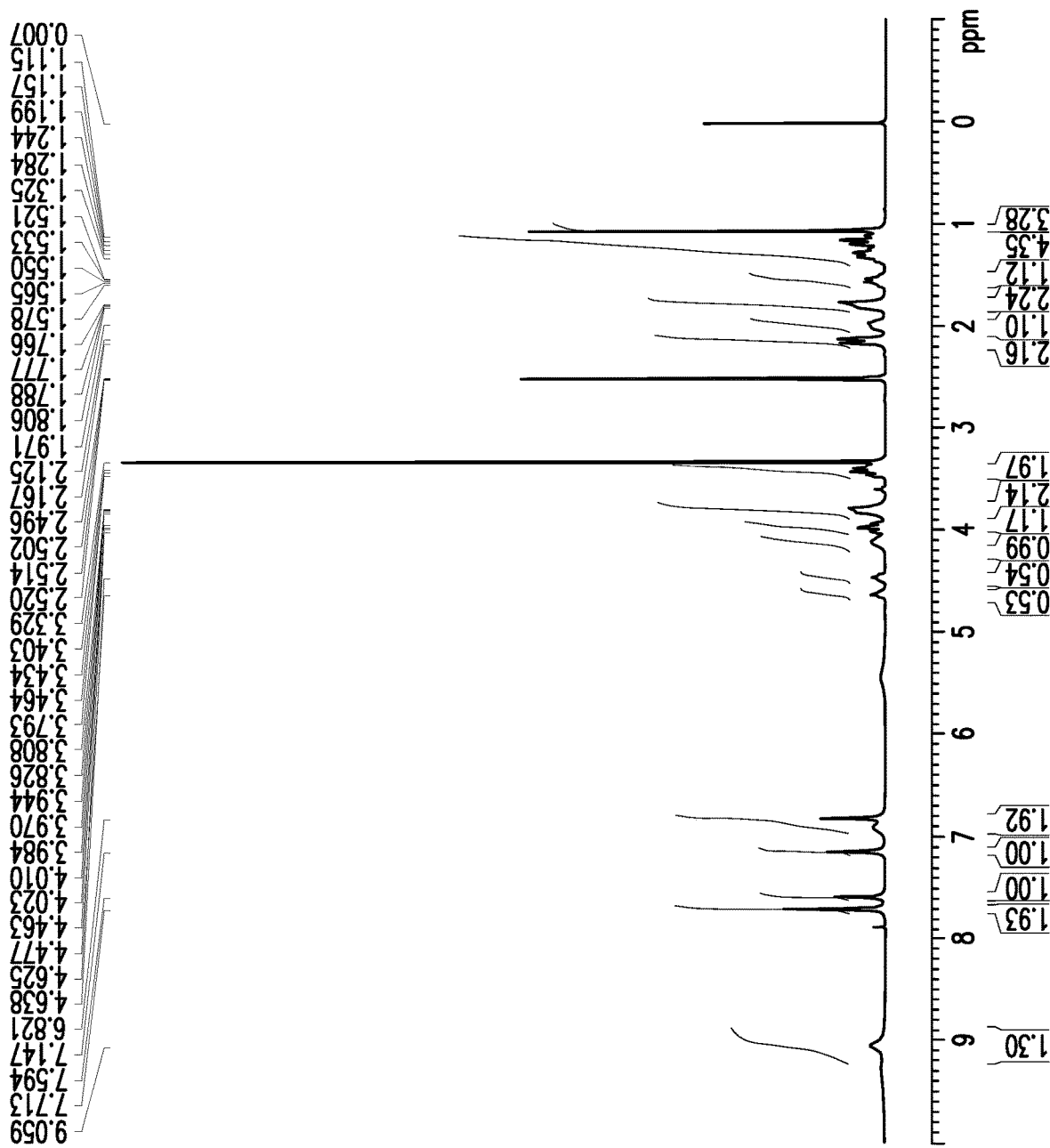

FIG. 10 provides a proton NMR spectrum for Compound 7.

Figure 11:
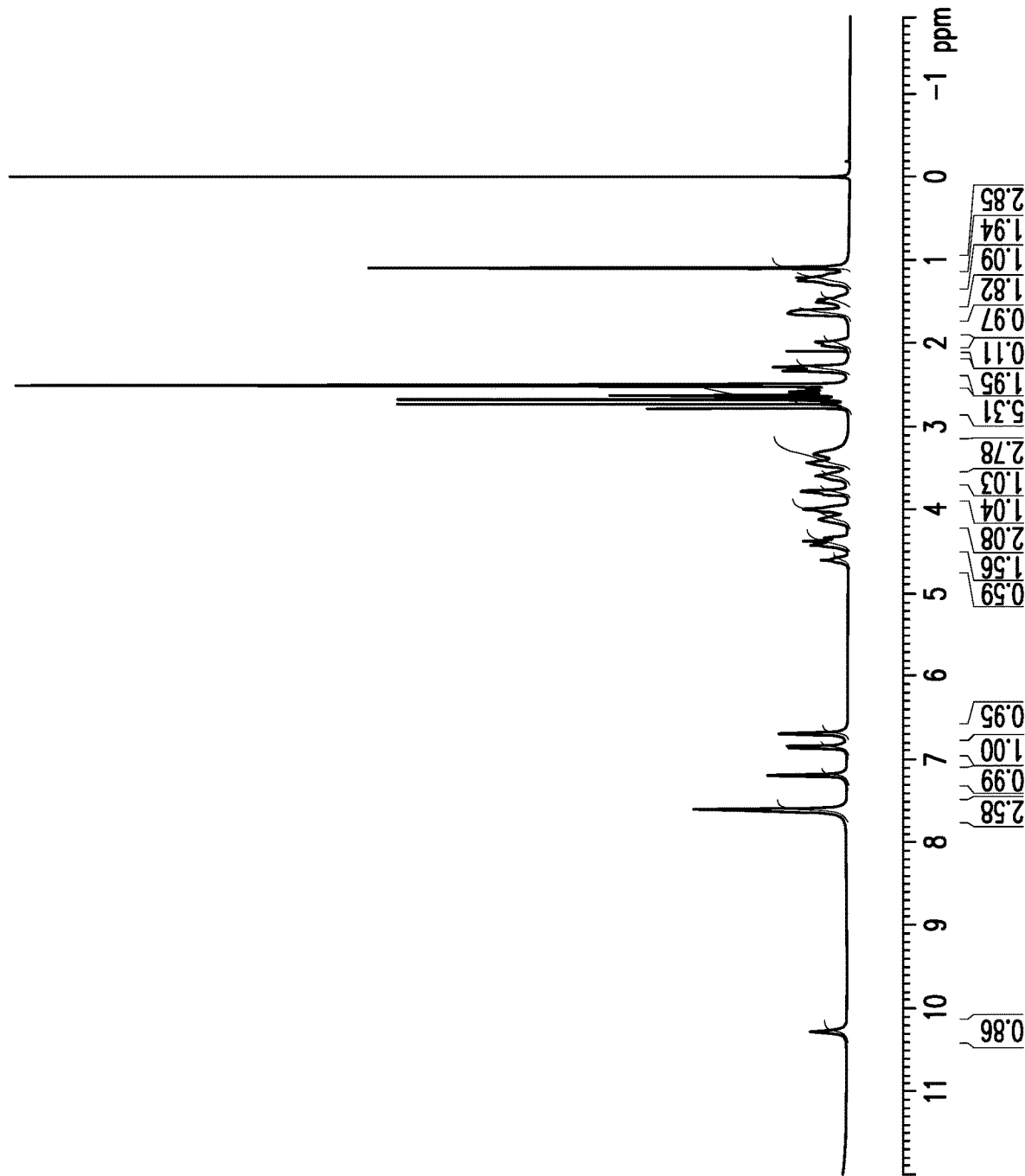

FIG. 11 provides a proton NMR spectrum for a compound of Formula (Ia).

5. DETAILED DESCRIPTION

5.1 Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein and unless otherwise indicated, the term "process(es)" provided herein refers to the methods provided herein which are useful for preparing a compound provided herein. Modifications to the methods provided herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, the term "transforming" refers to subjecting the compound at hand to reaction conditions suitable to effect the formation of the desired compound at hand.

As used herein, and unless otherwise indicated, the term "salt" includes, but is not limited to, salts of acidic or basic groups that may be present in the compounds provided herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, hydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

Unless otherwise indicated, the terms "enantiomerically enriched" and "enantiomerically pure," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In one embodiment, the compositions have about 99% by weight of one enantiomer relative to other enantiomer. In one embodiment, the compositions have greater than at least 99% by weight of one enantiomer relative to other enantiomer. In some embodiments, the enantiomerically enriched composition has a higher potency with respect to therapeutic utility per unit mass than does the racemic mixture of that composition.

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like) and carboxylate ions (e.g., acetate, ethanoate, propanoate, benzoate, glycerate, lactate, tartrate, glycolate, and the like). Counterions also include chiral counterions, some of which may be useful for chiral resolution of racemic mixtures. Exemplary chiral counterions include (S)-(+) mandelic acid, (D)-(+) tartaric acid, (+) 2,3-dibenzoyl-D-tartaric acid, N-Acetyl-L-leucine, and N-Acetyl-L-phenylalanine.

As used herein, and unless otherwise indicated, the terms "about" and "approximately" are used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

As used herein, and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiment, the value of XRPD peak position may vary by up to ±0.2 degrees 2θ while still describing the particular XRPD peak. As used herein, a tilde (i.e., "~") preceding a numerical value or range of values indicates "about" or "approximately."

As used herein, and unless otherwise indicated, the term "hydrogenation" refers to a chemical process that adds hydrogen atom to an unsaturated bond.

As used herein, and unless otherwise indicated, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom, and "natural isotopic composition" refers to the naturally occurring isotopic composition or abundance for a given atom.

The disclosure can be understood more fully by reference to the following detailed description and illustrative examples, which are intended to exemplify non-limiting embodiments.

Although most embodiments and examples provided herein are directed to the (5)-enantiomer of a compound, it is to be understood that the corresponding (R)-enantiomer of a compound can be prepared by the provided processes when the stereochemistry of chiral reactant, reagent, solvent, catalyst, ligand or the like is reversed.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, the compounds below may exhibit the following isomeric forms, which are referred to as tautomers of each other:

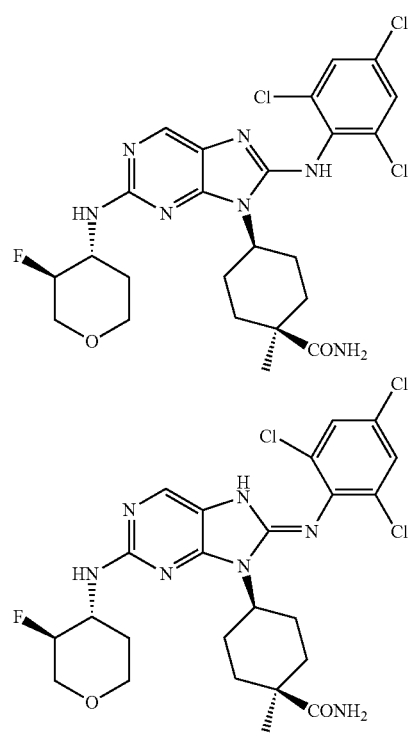

As readily understood by one skilled in the art, a wide variety of functional groups and other structures may exhibit tautomerism and all tautomers of compounds of formula (I) are within the scope of the present invention.

As used herein, and unless otherwise indicated, the term "ambient temperature" refers to a temperature range that is generally considered suitable for human occupancy, e.g., between about 15° C. and about 35° C. For example, the term "ambient temperature," where it is used in connection with reaction temperatures, denotes that the temperature range is between about 20° C. and about 30° C. In one embodiment, the term "ambient temperature," where it is used in connection with reaction temperatures, refers to about 25° C.

Finally, in general, the technical teaching of one embodiment can be combined with that disclosed in other embodiments provided herein.

5.2 Processes

Provided herein are processes for the preparation of a compound of Formula (I):

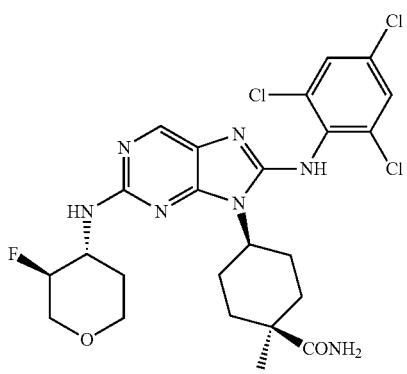

(I)

or a salt, solvate, hydrate, or isotopologue thereof. A compound of Formula (I) has the chemical name of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide. The processes comprise an optional step of preparing a salt of the compound of Formula (I).

In certain embodiments, the processes provided herein result in improved chiral purity for one or more intermediates and/or products throughout the route.

In one embodiment, provided herein are intermediate compounds used in or product compounds prepared by the processes provided herein, including solid forms (e.g., crystalline forms) thereof.

5.2.1 Process 1 for the Preparation of a Compound of Formula (I)

In one embodiment, provided herein is a process for preparing a compound of Formula (I):

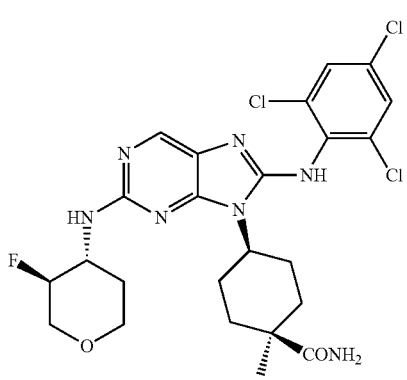

(I)

or a salt, solvate, hydrate, or isotopologue thereof, comprising (a) contacting Compound 1 of the formula:

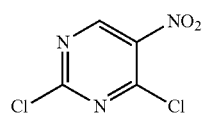

1 or a solvate, hydrate, or isotopologue thereof, with Compound 2 of the Formula:

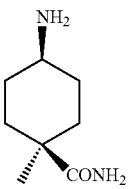

2 or a solvate, hydrate, or isotopologue thereof, to provide Compound 3 of the Formula:

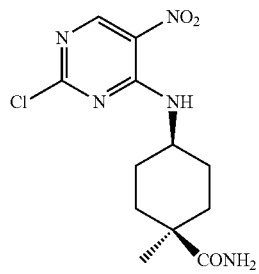

3 or a solvate, hydrate, or isotopologue thereof;

(b) contacting Compound 3, or a solvate, hydrate, or isotopologue thereof, with Compound 4 of the Formula:

4 or a solvate, hydrate, or isotopologue thereof to provide Compound 5 of the Formula:

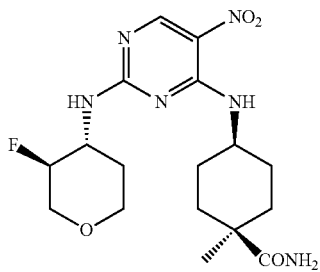

5 or a solvate, hydrate, or isotopologue thereof;

(c) reducing Compound 5, or a solvate, hydrate, or isotopologue thereof, to provide Compound 6 of the Formula:

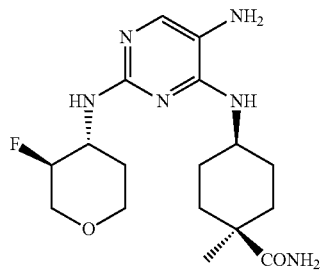

6 or a solvate, hydrate, or isotopologue thereof;

(d) contacting Compound 6 or a solvate, hydrate, or isotopologue thereof, with 2,4,6-trichlorophenyl isothiocyanate, to provide Compound 7 of the Formula:

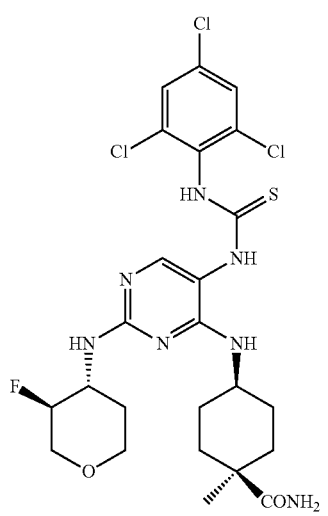

7 or a solvate, hydrate, or isotopologue thereof;

(e) contacting Compound 7 or a solvate, hydrate, or isotopologue thereof with ethylcarbodiimide hydrochloride, to provide a compound of Formula (I), or a solvate, hydrate, or isotopologue thereof; and (f) optionally converting the compound of Formula (I), or a solvate, hydrate, or isotopologue thereof, to a salt of the compound of Formula (I).

In one embodiment, provided herein is a process for preparing a compound of Formula (I):

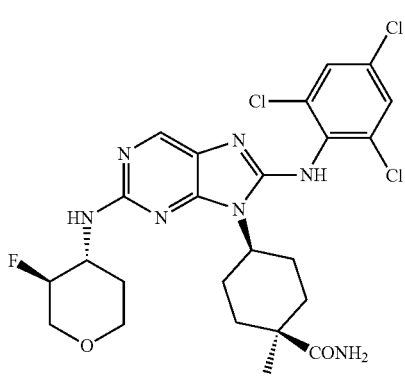

(I)

or a salt, solvate, hydrate, or isotopologue thereof, comprising (e) contacting Compound 7 or a solvate, hydrate, or isotopologue thereof with ethylcarbodiimide hydrochloride, to provide a compound of Formula (I), or a solvate, hydrate, or isotopologue thereof; and (f) optionally converting the compound of Formula (I), or a solvate, hydrate, or isotopologue thereof, to a citrate salt of the compound of Formula (I).

In one embodiment, provided herein is a process for preparing Compound 7:

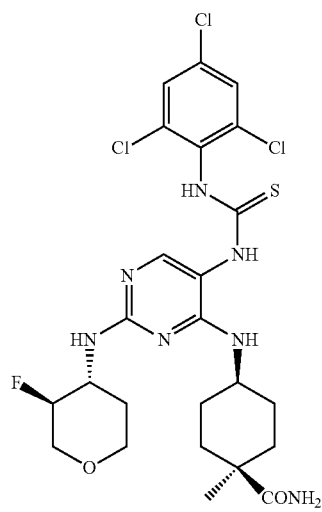

7 or a salt, solvate, hydrate, or isotopologue thereof, comprising (d) contacting Compound 6 or a solvate, hydrate, or isotopologue thereof, with 2,4,6-trichlorophenyl isothiocyanate.

In one embodiment, provided herein is a process for preparing Compound 6:

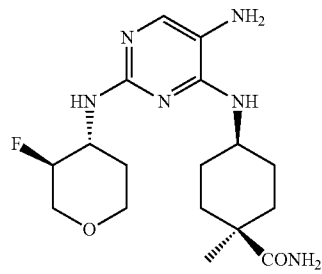

6 or a salt, solvate, hydrate, or isotopologue thereof, comprising (c) reducing Compound 5, or a solvate, hydrate, or isotopologue thereof.

In one embodiment, provided herein is a process for preparing Compound 5:

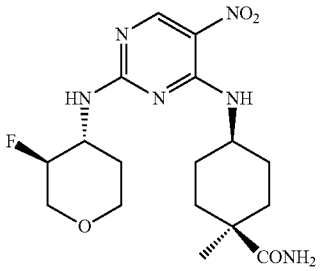

or a salt, solvate, hydrate, or isotopologue thereof, comprising (b) contacting Compound 3, or a solvate, hydrate, or isotopologue thereof, with Compound 4 or a solvate, hydrate, or isotopologue thereof.

In one embodiment, provided herein is a process for preparing Compound 3:

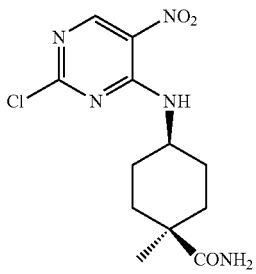

or a salt, solvate, hydrate, or isotopologue thereof, comprising (a) contacting Compound 1 of the Formula:

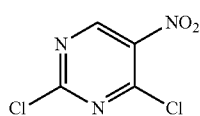

or a solvate, hydrate, or isotopologue thereof, with Compound 2 of the Formula:

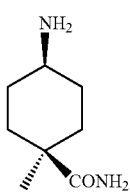

or a solvate, hydrate, or isotopologue thereof.

In one embodiment, step (a) comprises contacting Compound 1, or a salt, solvate, hydrate, or isotopologue thereof, with Compound 2, or a salt, solvate, hydrate, or isotopologue thereof in the presence of a base and in a solvent, under conditions suitable to provide Compound 3. In some embodiments, the base is potassium carbonate ($K_2CO_3$), N,N-diisopropylethylamine ("DIPEA"), triethylamine ("TEA"), or pyridine. In one embodiment, the base is $K_2CO_3$. In other embodiments, the solvent is dichloromethane ("DCM") or tetrahydrofuran ("THF"). In one embodiment, the solvent is THF. In some embodiments, a salt of Compound 2 is used. In some embodiments, the salt of Compound 2 is the benzenesulfonate salt. In some embodiments, the contacting is performed at about −5 to about 5° C., e.g., at about −3.0 to −2.4° C. or at about 0° C., and then warmed to about 20 to about 30° C., e.g., about 25° C. In some embodiments, step (a) comprises rinsing Compound 3 with heptanes.

In one embodiment, step (b) comprises contacting Compound 3, or a solvate, hydrate, or isotopologue thereof with Compound 4, in the presence of a base, in a solvent, under conditions suitable to provide Compound 5. In some embodiments, the base is DIPEA, TEA, or pyridine. In one embodiment, the base is DIPEA. In other embodiments, the solvent is DCM, THF, dioxane, N-methyl-2-pyrrolidone ("NMP") or DMF. In one embodiment, the solvent is THF. In some embodiments, the contacting is performed at elevated temperature, for example, from about 45° C. to about 60° C., e.g., at about 45.1 to about 46.2° C., at about 45 to about 52° C. or at about 50° C. In some embodiments, step (b) comprises adding water and seeds of Compound 5 at about 45 to about 60° C., e.g., about 51.7 to about 52° C., agitated, and adding additional water. In some embodiments, step (b) comprises adding water.

In one embodiment, step (c) comprises reducing Compound 5 or a solvate, hydrate, or isotopologue thereof with a reducing agent and a catalyst, in a solvent, under conditions suitable to provide Compound 6. In one embodiment, the reducing agent is $H_2$. In one embodiment, the reducing agent is $H_2$ at about 25 to about 35 psi, e.g., about 30 psi. In one embodiment, the catalyst is palladium on carbon (Pd/C). In some embodiments, the contacting is performed at about 35 to about 45° C., e.g., about 40° C. In some embodiments, following the contacting, the Pd/C is filtered and rinsed with the solvent. In one embodiment, the solvent is THF, water, MeOH or mixtures thereof. In one embodiment, the solvent is a mixture of THF and water. In some embodiments, step (c) comprises distilling under vacuum while maintaining a constant volume during distillation by the addition of acetonitrile.

In alternative embodiments, step (c) comprises reducing Compound 5 or a solvate, hydrate, or isotopologue thereof in the presence of a reducing agent and a base, in a solvent, under conditions suitable to provide Compound 6. In some embodiments, the reducing agent is $Na_2S_2O_4$. In some embodiments, the solvent is THF, water, or a mixture thereof. In some embodiments, the base is $NaHCO_3$.

In one embodiment, step (d) comprises contacting Compound 6 or a solvate, hydrate, or isotopologue thereof, with 2,4,6-trichlorophenyl isothiocyanate in a solvent, under conditions suitable to provide Compound 7. In some embodiments, solvent is THF, dimethylformamide ("DMF"), NMP, dioxane, acetonitrile, or ethanol ("EtOH"). In one embodiment, the solvent is THF. In some embodiments, the contacting is performed at about 20 to about 30° C., e.g., about 25° C.

In one embodiment, step (e) comprises contacting Compound 7 or a solvate, hydrate, or isotopologue thereof, with ethylcarbodiimide hydrochloride ("EDC HCl"), in a solvent, in the presence of a base, under conditions suitable to provide a compound of Formula (I). In some embodiments, the base is TEA. In one embodiment, the solvent is 2-methyltetrahydrofuran ("2-Me-THF"), THF, dioxane, NMP or DMF. In one embodiment, the solvent is 2-Me-THF. In some embodiments, the contacting is performed at about 55 to about 70° C., e.g., about 60 to about 70° C., about 60 or about 65° C. In some embodiments, step (e) comprises, after the contact, distilling off the solvent and adding acetonitrile. In some embodiments, step (e) comprises, after the contacting, adding seed crystals of a compound of Formula (I) at about 50° C. (e.g., about 49° C.) to about 55° C. and agitating for three hours, cooling to about 30 to about 40° C., about 15 to about 25° C. or about 20° C. for three hours, and washing with acetonitrile. In some embodiments, step (e) comprises adding acetonitrile.

In one embodiment, step (f) comprises contacting the compound of Formula (I) or a solvate, hydrate, or isotopologue thereof, with an acid, in a solvent, under conditions suitable to provide a salt of a compound of Formula (I). In some embodiments, the salt of a compound of Formula (I) is the citrate salt, the HCl salt, the sulfate salt, or the mesylate salt. In some embodiments, the acid is citric acid, HCl, sulfuric acid, or methanesulfonic acid. In some embodiments, the salt of a compound of Formula (I) is the citrate salt and the acid is citric acid. In one embodiment, the solvent is acetone, water, or a mixture thereof. In some embodiments, the contacting is performed at about 35 to about 45° C., e.g., at about 37 to about 43° C. or about 40° C. In some embodiments, step (f) comprises adding seed crystals of the salt of the compound of Formula (I). In some embodiments, step (f) further comprises adding water and agitating at about 35 to about 45° C., e.g., at about 37 to about 43° C. or about 40° C. In some embodiments, the salt is a citrate salt. Citrate salts of the compound of Formula (I) are described in U.S. application Ser. No. 15/475,836. In some embodiments, the citrate salt of the compound of Formula (I) is Citrate Form Z, described in U.S. application Ser. No. 15/475,836.

6. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Organic Chemistry. Unless otherwise specified, the water content in a compound provided herein is determined by Karl Fisher (KF) method.

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

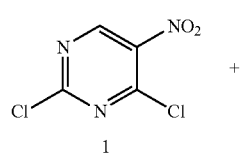

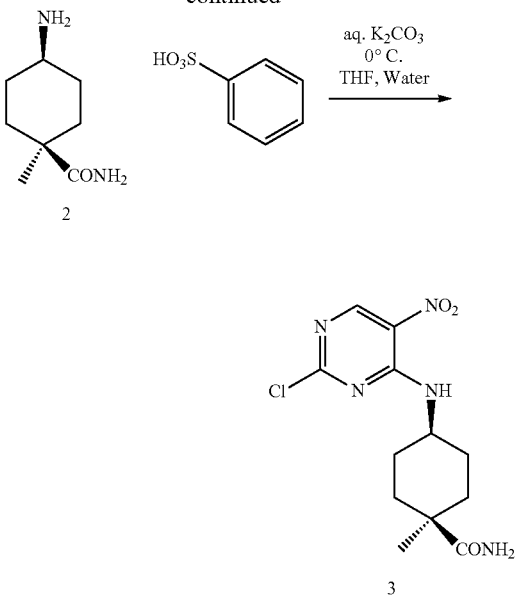

Compound 2 (10 kg, 31.8 mol) and Compound 1 (7.4 kg, 38.2 mol) were slurried in THF. The slurry was cooled to 0±5° C. Potassium carbonate aqueous solution was prepared and added to the THF slurry while maintaining a temperature at 0±5° C. (e.g., −2.4° C. to −3.0° C.). The batch was agitated at 0±5° C. for at least 2 hours, and was then warmed to 25±5° C. over at least 60 minutes, and agitated at 25±5° C. for at least 12 hours (e.g., 16 hours). The reaction completion was confirmed by high performance liquid chromatography (HPLC). Water was added to the batch, and the mixture was agitated at 25±5° C. for at least 4 hours before being filtered. The collected solid was washed with a THF/Water (e.g., ⅓ volume ratio) mixture, dried, and isolated to provide Compound 3 (6.85 kg, 68.5% yield). FIG. 1 provides a representative differential scanning calorimetric (DSC) thermogram of Compound 3. FIG. 8 provides a proton NMR spectrum for Compound 3.

Example 2

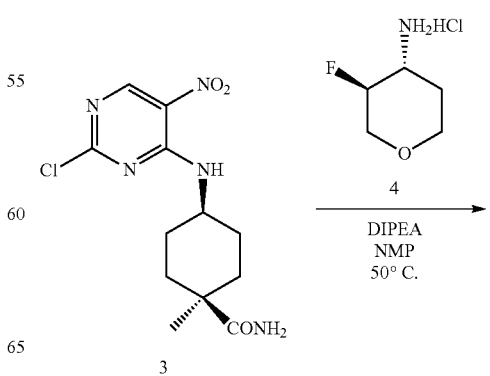

Compound 3 (6.8 kg, 21.7 mol) and Compound 4 (3.5 kg, 22.8 mol) were mixed with THF at 25±5° C. The mixture was heated to 50±5° C. DIPEA was then charged to the THF mixture while maintaining the batch temperature at 45-60° C. (e.g., 45.1° C. to 46.2° C.). The batch was agitated at 50±5° C. (e.g., 45° C. to 52° C.) for at least 12 hours (e.g., 20 hours). The reaction completion was confirmed by HPLC. Water was charged to the batch while maintaining the batch temperature at 45-60° C. (e.g., 51.7° C. to 52° C.). Compound 5 seed was charged, the mixture was agitated at 50±5° C. for at least 2 hours, and water was added to the batch at a rate no faster than 3 L/h while maintaining the batch temperature at 45-60° C. After being agitated at 50±5° C. for at least 3 hours, the mixture was cooled to 25±5° C. over at least 2 hours, agitated at 25±5° C. for at least 12 hours, and filtered. The wet cake was washed twice with a THF/water mixture and dried at 45±5° C. to offer Compound 5 (8.1 kg, 94.2% yield). FIG. 2 provides a representative DSC thermogram of Compound 5. FIG. 9 provides a proton NMR spectrum for Compound 5.

Example 3

A mixture of Compound 5 (7.7 kg, 19.4 mol) and Pd/C in THF and water was hydrogenated at 30±5 psi and 40±5° C. for at least 7 hours (e.g., 19 hours). The reaction completion was confirmed by HPLC. After being cooled to 25±5° C. (e.g., ambient temperature), the catalyst was filtered and the filter pad rinsed twice with THF/water. Sodium chloride (solid) was charged to the filtrate containing the batch, and the mixture was agitated until the solids were dissolved. The phases were separated, and the batch was reduced to ~10× volumes via vacuum distillation at less than 45° C. Water content was reduced to no more than 1% by vacuum distillation at constant volume with addition of acetonitrile at less than 45° C.

The batch was cooled to 25±5° C. (e.g., ambient temperature) and 2,4,6-trichlorophenyl isothiocyanate (5.1 kg, 21.3 mol) and THF were charged. The mixture was agitated at ambient temperature for at least 16 hours (e.g., 17 hours) and filtered. The filter cake was washed twice with acetonitrile and dried (e.g., dried at 35 to 45° C. under vacuum with nitrogen purge until loss on drying ("LOD") was less than or equal than 1%) to provide Compound 7 (10.3 kg, 88% yield). FIG. 3 provides a representative DSC thermogram of Compound 7. FIG. 10 provides a proton NMR spectrum for Compound 7.

Example 4

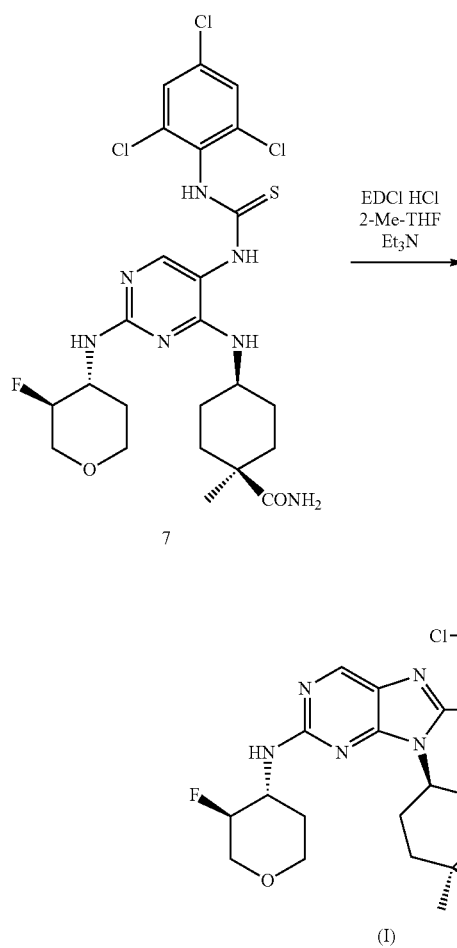

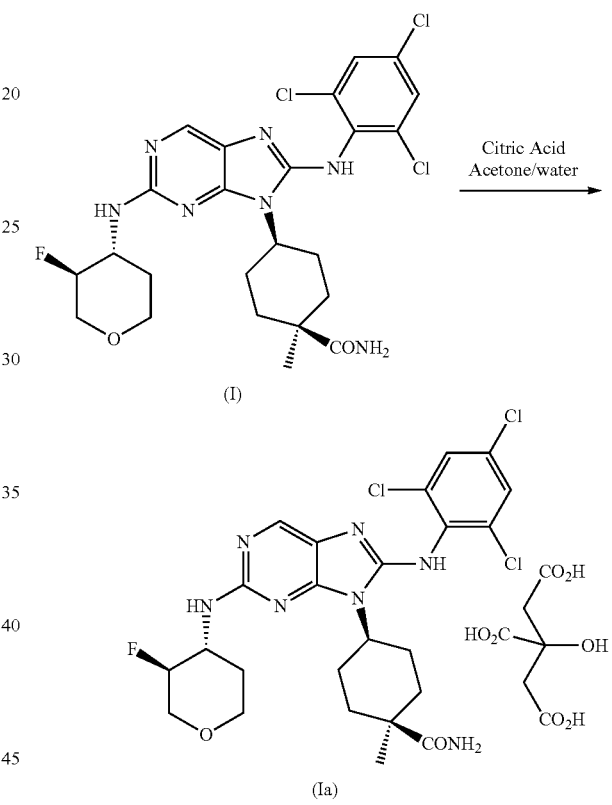

To a mixture of Compound 7, EDCI HCl, and 2-Me-THF was charged TEA, and the batch was heated to 65±5° C. over at least 1 h and agitated at 65±5° C. for at least 4 hours (e.g., 4 hours). The reaction completion was checked by HPLC. The batch was cooled to 25±5° C. (e.g., ambient temperature) and filtered. The filtrate containing the batch was washed twice with 20 wt % NH$_4$Cl solution and once with water. The batch was filtered and the filter rinsed with 2-Me-THF. The batch was distilled to ~10× volumes under vacuum at 45±10° C. and further distilled at constant volume at 45±10° C. with addition of acetonitrile until the 2-Me-THF content was ≤30 vol % (e.g., 10-30 vol % or 20-30 vol %, by NMR).

The batch was held at 49 to 55° C. and treated with Formula (I) seed. The mixture was held at 49 to 55° C. for at least one hour, and distilled at constant volume at 45±10° C. with addition of acetonitrile until the 2-Me-THF content was 5-10 vol % (e.g., 7%, by NMR). The batch was held at 49 to 55° C. for at least 3 h, cooled to 35±5° C. over at least 1 h, held at 35±5° C. for at least 3 hours, cooled to 20±5° C. over about at least 1 h, and agitated at 20±5° C. for at least 3 hours. The batch was filtered, washed three times with acetonitrile, and dried. The wet cake was dried at 40 to 50° C. under vacuum with moisturized nitrogen purge until monohydrate was formed and residual acetonitrile content was not more than 410 ppm. The sample was dried for more than 80 hours. Further drying was conducted without humidification and the temperature was increased to 60±5° C. to reduce the acetonitrile level to within the specification limit (5 ppm acetonitrile), to provide a compound of Formula (I) as the anhydrous form (6.7 kg, 78.8% yield). FIG. 4 provides a representative DSC thermogram of a compound of Formula (I). FIG. 5 provides a Nuclear Magnetic Resonance (NMR) spectrum for a compound of Formula (I).

Alternatively, the compound of Formula (I) can be dried under a humidified stream of nitrogen to obtain a monohydrate form.

Example 5

Citric acid (2.8 kg, 14.7 mol) was dissolved in 22.7 kg of acetone/water (80/20 v/v) and heated to 40±3° C. The compound of Formula (I) (6.0 kg, 10.5 mol) was dissolved in 37.3 kg of acetone/water (80/20 v/v) at 30±5° C. until a solution formed and cooled to 20±5° C. About 3.3% by volume of the compound of Formula (I) solution (1.53 kg) was added to the reactor over 10 to 20 minutes keeping the batch at 40±3° C. A citrate salt of the compound of Formula (I) seed (e.g., 46.5 g) was charged to the reactor, and the batch was held at 40±3° C. for at least 30 min. The batch was held at 40° C. for at least additional 30 minutes before the remaining solution of the compound of Formula (I) in acetone/water was charged to the reactor over at least 5 hours, and the batch was agitated at 40±3° C. (e.g., 40° C.) for at least 3 hours until Form B was confirmed by XRPD.

Water (25.4 kg) was charged to the batch over about 5 hours maintaining a batch temperature of 40±5° C. The batch was agitated at 40±5° C. (e.g., 40° C.) for at least one hour until Form B was confirmed by XRPD. The batch was cooled to 20±5° C. (e.g., 20° C.) over about 3 hours, agitated at 20±5° C. (e.g., 20° C.) for at least 1 hour, and filtered. The filter cake was washed with an acetone/water mixture and water, and dried to provide a compound of Formula (Ia) (7.7 kg, 96.3% yield). FIG. 6 provides a representative DSC thermogram for the compound of Formula (Ia). FIG. 7 provides a representative XRPD pattern of the compound of Formula (Ia). FIG. 11 provides a proton NMR spectrum for a compound of Formula (Ia).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

All of the patents, patent applications and publications referred to herein are incorporated herein in their entireties. Citation or identification of any reference in this application is not an admission that such reference is available as prior art to the claimed subject matter.

What is claimed is:

1. A process for preparing a crystalline salt form comprising a compound of Formula (I) and citric acid:

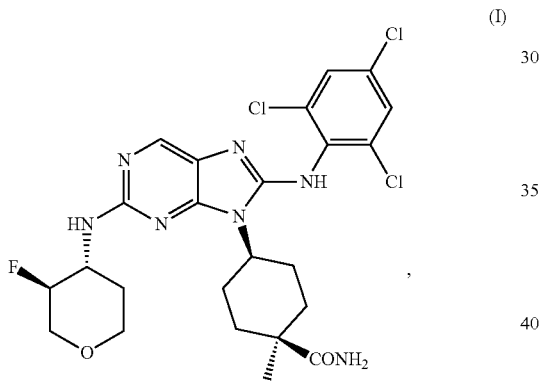

(I)

comprising
(a) contacting Compound 1 of the formula:

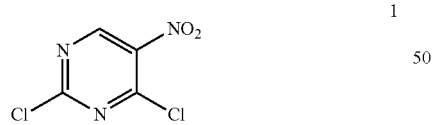

1 or a salt, solvate, or hydrate thereof, with Compound 2 of the Formula:

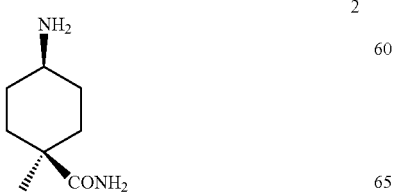

2 or a salt, solvate, or hydrate thereof, to provide Compound 3 of the Formula:

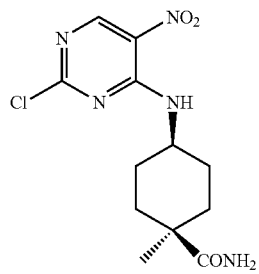

3 or a solvate, or hydrate thereof;
(b) contacting Compound 3, or a solvate, or hydrate thereof, with Compound 4 of the Formula:

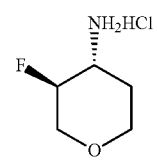

4 or a solvate, or hydrate thereof, to provide Compound 5 of the Formula:

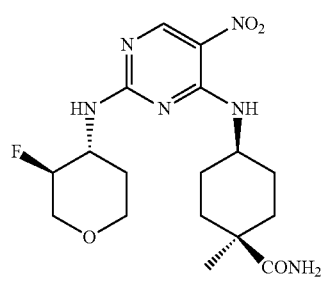

5 or a solvate, or hydrate thereof;
(c) reducing Compound 5, or a salt, solvate, or hydrate thereof with a reducing agent and a catalyst, to provide Compound 6 of the Formula:

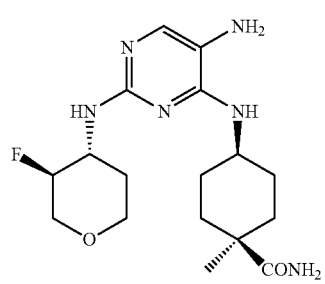

6 or a solvate, or hydrate thereof;
(d) contacting Compound 6 or a salt, solvate, or hydrate thereof, with 2,4,6-trichlorophenyl isothiocyanate, to provide Compound 7 of the Formula:

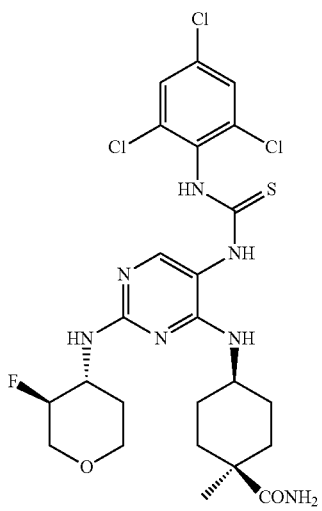

or a solvate, or hydrate thereof;

(e) contacting Compound 7 or a solvate, or hydrate thereof with ethylcarbodiimide hydrochloride, to provide a compound of Formula (I), or a solvate, or hydrate thereof; and (f) converting the compound of Formula (I), or a solvate, or hydrate thereof, to said crystalline salt form, wherein said crystalline salt form has an X-ray powder diffraction pattern substantially as shown in FIG. 7.

2. The process of claim 1, wherein the contacting in step (a) is in the presence of a base.

3. The process of claim 1, wherein the contacting in step (a) is in a solvent.

4. The process of claim 2, wherein the base in step (a) is potassium carbonate.

5. The process of claim 3, wherein the solvent in step (a) is tetrahydrofuran.

6. The process of claim 1, wherein the salt of Compound 2 is a benzenesulfonate salt.

7. The process of claim 1, wherein the contacting in step (b) is in the presence of a base.

8. The process of claim 1, wherein the contacting in step (b) is in a solvent.

9. The process of claim 7, wherein the base is N—N-diisopropylethylamine.

10. The process of claim 8, wherein the solvent is tetrahydrofuran.

11. The process of claim 1, wherein the reducing agent in step (c) is H2.

12. The process of claim 1, wherein the catalyst in step (c) is Pd/C.

13. The process of claim 1, wherein the reducing in step (c) is in a solvent.

14. The process of claim 13, wherein the solvent is a mixture of tetrahydrofuran and water.

15. The process of claim 1, wherein the contacting in step (d) is in a solvent.

16. The process of claim 15, wherein the solvent is tetrahydrofuran.

17. The process of claim 1, wherein the contacting in step (e) is in the presence of a base.

18. The process of claim 17, wherein the base is triethylamine.

19. The process of claim 1, wherein the contacting in step (e) is in a solvent.

20. The process of claim 19, wherein the solvent is 2-methyltetrahydrofuran.

21. The process of claim 1, wherein the converting in step (f) comprises contacting the compound of Formula (I), or a solvate, or hydrate thereof with citric acid.

* * * * *